United States Patent

Nilsson et al.

Patent Number: 5,698,516
Date of Patent: Dec. 16, 1997

[54] BIOLOGICALLY ACTIVE VASOPRESSIN ANALOGUES

[75] Inventors: Anders Nilsson; Håkan Olson, both of Lund; Christina Söderberg-Ahlm, Malmö; Jerzy Trojnar, Bunkeflostrand, all of Sweden

[73] Assignee: Ferring B.V., Hoofddorp, Netherlands

[21] Appl. No.: 553,555

[22] PCT Filed: Jun. 16, 1994

[86] PCT No.: PCT/SE94/00594

§ 371 Date: Dec. 18, 1995

§ 102(e) Date: Dec. 18, 1995

[87] PCT Pub. No.: WO95/00548

PCT Pub. Date: Jan. 5, 1995

[30] Foreign Application Priority Data

Jun. 18, 1993 [SE] Sweden ................... 9302124

[51] Int. Cl.$^6$ ............ A61K 38/00; A61K 38/11; C07K 5/00; C07K 7/00
[52] U.S. Cl. ............ 514/11; 514/807; 514/866; 930/21; 930/150; 530/315
[58] Field of Search ............ 514/11, 807, 866; 930/21, 150; 530/315

[56] References Cited

FOREIGN PATENT DOCUMENTS

| 0037516 | 10/1981 | European Pat. Off. |
| 0115379 | 8/1984 | European Pat. Off. |
| 27 23 453 | 12/1977 | Germany |

OTHER PUBLICATIONS

Journal of Medicinal Chemistry, vol. 18, No. 8, 1975, Clark W. Smith, et al. p. 822–825.

*Primary Examiner*—Robert J. Hill, Jr.
*Assistant Examiner*—Jennifer Harle
*Attorney, Agent, or Firm*—Oblon, Spivak, McClelland, Maier & Neustadt, P.C.

[57] ABSTRACT

Vasopressin analogues of formula (I)

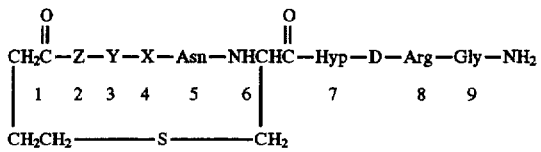

wherein X is (S)-2-amino-2-methyl-butanoic acid (CaMeAbu) or Valine (Val), Y is Thienylalanine (Thi) or Methionine (Met), Z is D-Phenylalanine (D-Phe) or D-Thienylalanine (Thi) or D-Tyrosine (D-Tyr), are disclosed. Pharmaceutical preparations comprising a vasopressin analogue of the invention as active ingredient are disclosed and exemplified by oral preparations, nasal preparations, and intravenous preparations. The vasopressin analogues of the invention are intended for use as a medicament, specially an antidiuretic agent. The antidiuretic agent is preferably used for the treatment of diabetes insipidus or enuresis.

6 Claims, No Drawings

BIOLOGICALLY ACTIVE VASOPRESSIN ANALOGUES

The present invention relates to biologically active vasopressin analogues. More precisely, the invention relates to vasopressin analogues having specific antidiuretic activity and much improved bioavailability compared to the widely used antidiuretic compound 1-desamino-8-D-arginine vasopressin, also known as desmopressin or DDAVP.

BACKGROUND

DDAVP has now been on the market for about 20 years as a pharmaceutical preparation with antidiuretic activity, at first mainly for the treatment of patients suffering from diabetes insipidus, but, since a few years, also for the treatment of enuresis, specially nocturnal enuresis. It has also successfully been used in the treatment of hemphilia type A, yon Willebrand's disease and prolonged bleeding times of unknown reasons.

The intravenous administration of DDAVP gives the best bioavailability of the compound, but is inconvenient to use at home. Therefore, a common way of administration of DDAVP has been by intranasal route. However, the bioavailability of the compound decreases about 10 times. DDAVP may also be administered orally as is disclosed in the European Patent No. 0 163 723. However, the loss in bioavailability is even greater than by administration through the nasal mucosa.

Research efforts have been focused on improved DDAVP analogues. Numerous DDAVP derivatives have been synthesized and tested for bioavailability in the search for compounds with specific antidiuretic activity and with improved absorption through the nasal mucosa and absorption through the intestinal mucosa.

DESCRIPTION OF THE INVENTION

The present invention provides new vasopressin analogues of the formula $$\begin{array}{c} \overset{O}{\underset{\|}{\text{CH}_2\text{C}}}-Z-Y-X-\text{Asn}-\overset{O}{\underset{\|}{\text{NHCHC}}}-\text{Hyp}-D-\text{Arg}-\text{Gly}-\text{NH}_2 \\ |\phantom{xxx}1\phantom{xx}2\phantom{xx}3\phantom{xx}4\phantom{xx}5\phantom{xx}6\phantom{xxxx}|\phantom{xxx}7\phantom{xxx}8\phantom{xxx}9 \\ \text{CH}_2\text{CH}_2\text{——S——CH}_2 \end{array}$$

wherein X is (S)-2-amino-2-methyl-butanoic acid (CαMeAbu) or Valine (Val),

Y is Thienylalanine (Thi) or Methionine (Met),

Z is D-Phenylalanine (D-Phe) or D-Thienylalanine (Thi) or D-Tyrosine (D-Tyr)

and Asn is Asparagine Hyp is 4-trans-Hydroxyproline D-Arg is D-Arginine Gly is Glycine.

As is evident from the testing of biological activity disclosed later in the text, the new compounds of the invention have, in addition to good antidiuretic activity, about 12 to 25 times higher values for gastrointestinal absorption than DDAVP, and 2 to 5 times higher intranasal absorption values. The blood clotting effect of the compounds of the invention has not yet been tested, but it is believed that in analogy with DDAVP, the compounds of the invention will also be useful for the treatment of hemphilia type A, yon Willebrand's disease and prolonged bleeding times of unknown reasons.

Another aspect of the invention is directed to a pharmaceutical preparation comprising a vasopressin analogue of the invention as active ingredient. This aspect of the invention is intended to comprise any useful pharmaceutical preparation as long as it contains a vasopressin analogue of the invention as active ingredient. The pharmaceutical preparation is preferably in the form of an oral preparation, such as a tablet or capsule, a nasal preparation, such as a nasal spray or nasal drops, or an intravenous preparation, such as an injectable solution. In a pharmaceutical preparation the active ingredient is in combination with pharmaceutically acceptable additives and/or diluents. A suitable pharmaceutically acceptable diluent is isotonic saline solution. As to the other pharmaceutically acceptable additives and diluents, such can be found in the literature, e.g. the European or US Pharmacopoeia, and these additives shall be chosen in conformity with the specific form of the preparation for a specific administration route.

A further aspect of the invention is directed to a vasopressin analogue of the invention for use as a medicament. The medicament is preferably an antidiuretic agent.

Another aspect of the invention is directed to the use of a vasopressin analogue according to the invention for the preparation of a medicament for the treatment of diabetes insipidus. The invention also comprises the use of a vasopressin analogue according to the invention for the preparation of a medicament for the treatment of enuresis, specially nocturnal enuresis.

Yet another aspect of the invention is directed to a method of treating a diabetes insipidus or enuresis patient comprising administering to said patient an antidiuretically effective amount of a vasopressin analogue of the invention or a pharmaceutical preparation of the invention.

GENERAL DESCRIPTION OF THE SYNTHESIS

The vasopressin (VP) analogues of the invention may be prepared in accordance with known strategies for synthesizing peptides, i.e. step by step, by forming peptide bonds between amino acid residues or modified residues and final ring closure in order to complete the synthesis.

All the VP analogues prepared in the examples given below were synthesized by solid phase technique (J. M. Stewart, J. D. Young, Solid Phase Peptide Synthesis, Pierce Chemical Company, 1984; and E. Atherton, R. C. Sheppard, Solid Phase Peptide Synthesis, 1989).

The peptides were purified by reversed phase chromatography with a mobile phase consisting of acetonitrile/water/ 0.1% TFA. The pure peptides were then converted to their acetate-salts. The purity and structure of the peptides were confirmed by HPLC, amino acid analysis and FAB-MS.

The following abbreviations have been used:

Boc=t-butyloxycarbonyl

Fmoc=fluorenylmethyloxycarbonyl

H-CαMeAbu-OH=(S)-2-amino-2-methyl-butanoic acid

Hyp=4-trans-hydroxyproline

Thi=2-thienylalanine

TBTU=2-(1H-benzotriazole-1-yl)-1,1,3,3-tetramethyluronium tetrafluoroborate

DMF=dimethylformamide

TFA=trifluoroacetic acid

The amino acid derivatives were supplied by Bachem AG, Switzerland, except (S)-2-amino-2-methyl-butanoic acid (H-CαMeAbu-OH) which was supplied by Janssen Chimica (art.nr. 29.005.02). The Fmoc-group was introduced by standard methods (P.B.W. Ten Kortenaar et al., Int. J. Peptide Protein Res. 27, 1986, 398), and NαFmoc-S-(3-t-butyloxycarbonyl propyl)-cysteine was synthesized following the proceeding published by Z. Procházka et al., Collect. Czech. Chem. Commun., 57, 1992, 1335.

The reference compound DDAVP was synthesized by Ferring AB, Malmö, Sweden, in known manner, and the reference compound of Example 3 was also synthesized by Ferring AB, Malmö, Sweden. The last mentioned compound has been disclosed by M. Zaoral et al. in Peptides 1986, p. 468 Table 2. (1987 Walter de Gruyter & Co., Berlin, N.Y.).

EXAMPLE 1

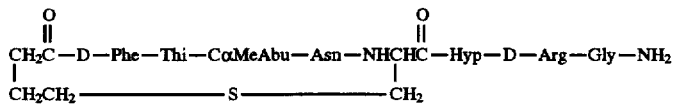

The peptide was synthesized with the solid phase technique. Fmoc/tBu-strategy was used, except for Position 2 (D-Phe), where Nα-Boc-amino acid (Boc-D-Phe-OH) was utilized as a derivative. TentaGel-S RAM-resin (1 g, 0.2 mmol/g; RAPP Polymere S 30 023) was used as solid phase. The peptide was cleaved from the resin and deprotected with TFA/ethanedithiol/anisole 95:2.5:2.5 (1.5 h; room temperature). Most of the liquid was evaporated and the peptide was precipitated with diethylether and then freeze-dried from water. The cyclization between positions 1 and 2 was performed in dry DMF with TBTU (1–2 eqv) and N-methyl-morpholine (15–20 eqv). The concentration of the peptide was 1 mg/ml. Reaction time was 4 hours at room temperature. The solvent was evaporated and the peptide was precipitated with diethylether. Purification was performed on a reversed-phase column with acetonitrile/water/ 0.1% TFA as an eluent. The fractions of acceptable purity were evaporated and the residue attached to a reversed-phase column. The column was washed with 0.2 M ammonium acetate and water. The peptide was eluted with a mixture of acetonitrile/water/1% acetic acid. Fractions of acceptable purity were evaporated and freeze-dried. The peptide structure was confirmed by HPLC, amino acid analysis and FAB-MS analysis.

Yield 36 mg, 99% purity.

EXAMPLE 2

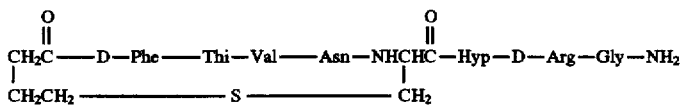

The peptide was synthesized and purified by using the same strategy as in Example 1.

Yield 77 mg, 99% purity.

EXAMPLE 3 (Reference)

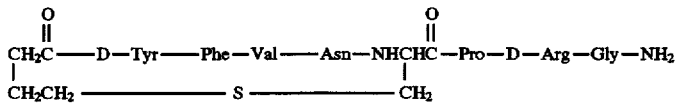

The peptide was synthesized and purified by using the same strategy as in Example 1.

Yield 23 mg, 99% purity.

EXAMPLE 4

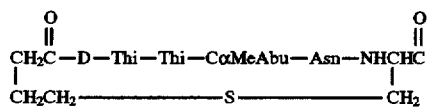

The peptide was synthesized and purified by using the same strategy as in Example 1.

Yield 30 mg, 99% purity.

EXAMPLE 5

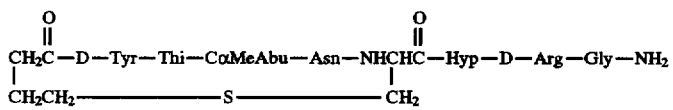

The peptide was synthesized and purified by using the same strategy as in Example 1.

Yield 34 mg, 99% purity.

EXAMPLE 6

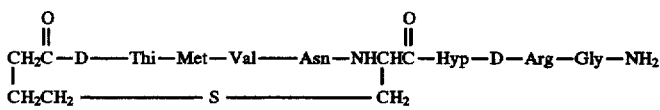

The peptide was synthesized and purified by using the same strategy as in Example 1.

Yield 57 mg, 99% purity.

Biological activity

Compounds were investigated in vivo for the following characteristics:

a) Antidiuretic activity ($AD_{iv}$)

The antidiuretic activity of the peptides was determined in the well established rat model which is based on continuous measurement of the conductivity of the urine produced by the rat after an intravenous challenge with peptide (J. Medicinal Chem. (1978), 21, 352–356).

b) Gastrointestinal absorption of peptides [$(F_{AD})_V$]

Absorption of peptides administered in the intestine through a surgically introduced plastic tube (10 cm distal of pylorus) was determined by comparing the antidiuretic effect (area under curve) after intestinal administration with the antidiuretic effect after intravenous adminstration. The antidiuretic effect was followed as described (J. Medicinal Chem. (1978) 21, 352–356).

c) Intranasal absorption of peptides $(F_{AD})_{in}$

Absorption of peptides administered in a volume of 30 μl in the nasal cavity through a PE20 cannula attached to a Hamilton syringe (introduced 10 mm without surgery), was determined by comparing the antidiuretic effect (area under curve) after intranasal administration with the antidiuretic effect after intravenous administration. The antidiuretic effect was followed as described (J. Medicinal Chem. (1978) 21, 352–356).

Results:

| Compound | $AD_{iv}$ [IU/μmol] | $(F_{AD})_V$ [%] | $(F_{AD})_{in}$ [%] |
|---|---|---|---|
| Ex. 1 | 631 | 1.3 | 42 |
| Ex. 2 | 1026 | 1.2 | 20 |
| Ex. 3 (Reference) | 1530 | 0.4 | 5 |
| Ex. 4 | 984 | 2.5 | 22 |
| Ex. 5 | 911 | 1.4 | 17 |
| Ex. 6 | 700 | 1.6 | 22 |
| DDAVP (Reference) | 1100 | 0.09 | 8 |

It is evident that the reference compound DDAVP and that of Example 3 have a far lower bioavailability than the compounds of the invention (Ex. 1, Ex. 2, Ex. 4, Ex. 5 and Ex. 6).

We claim:

1. A vasopressin analogue of the formula

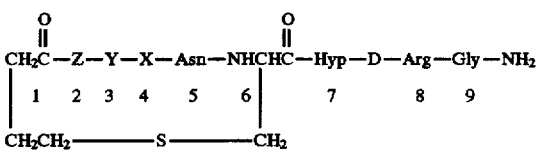

wherein X is (S)-2-amino-2-methyl-butanoic acid (CαMeAbu) or Valine (Val),

Y is Thienylalanine (Thi) or Methionine (Met),

Z is D-Phenylalanine (D-Phe) or D-Thienylalanine (Thi) or D-Tyrosine (D-Tyr)

and Asn is Asparagine Hyp is 4-trans-Hydroxyproline

D-Arg is D-Arginine Gly is Glycine.

2. A pharmaceutical preparation comprising a vasopressin analogue according to claim 1 as active ingredient and a pharmaceutically acceptable carrier or diluent.

3. A pharmaceutical preparation according to claim 2, in the form of an oral preparation.

4. A pharmaceutical preparation according to claim 2, in the form of a nasal preparation.

5. A pharmaceutical preparation according to claim 2, in the form of an intravenous preparation.

6. A method of treating a diabetes insipidus or enuresis patient comprising administering to said patient an antidiuretically effective amount of a vasopressin analogue according to claim 1 or a pharmaceutical preparation thereof.

* * * * *